United States Patent [19]

Stock

[11] Patent Number: 5,713,871
[45] Date of Patent: Feb. 3, 1998

[54] PROTECTIVE SLEEVE FOR HYPODERMIC NEEDLE

[76] Inventor: David M. Stock, 2108 Hadden Rd., Walnut Creek, Calif. 94596

[21] Appl. No.: 699,132

[22] Filed: Aug. 16, 1996

[51] Int. Cl.⁶ .................................................. A61M 5/32
[52] U.S. Cl. ........................ 604/192; 604/198; 604/263
[58] Field of Search ............................. 604/264, 263, 604/198, 187, 110, 218, 227, 192

[56] References Cited

U.S. PATENT DOCUMENTS

| | | | |
|---|---|---|---|
| 4,484,915 | 11/1984 | Tartaglia | 604/227 |
| 4,915,699 | 4/1990 | Kornberg | 604/198 X |
| 5,026,353 | 6/1991 | Bartman | 604/263 X |
| 5,135,510 | 8/1992 | Maszkiewicz et al. | 604/198 X |
| 5,300,040 | 4/1994 | Martin | 604/263 X |

*Primary Examiner*—John D. Yasko
*Attorney, Agent, or Firm*—Bielen, Peterson & Lampe

[57] ABSTRACT

A hypodermic needle having a rigid, clear, protective sleeve encircling the perimeter of the barrel of the hypodermic needle and connected to the plunger of the hypodermic needle, the protective sleeve being drawn toward the bevel of the hypodermic needle as the plunger is depressed. Additionally, the preferred embodiment includes a locking device that locks the protective sleeve in place once the plunger is fully depressed and the injection is complete, preventing reuse of the hypodermic needle and reducing the chance of accidental contact with the bevel.

9 Claims, 2 Drawing Sheets

PROTECTIVE SLEEVE FOR HYPODERMIC NEEDLE

BACKGROUND OF THE INVENTION

This invention relates generally to a protective sleeve for a syringe or hypodermic needle having a projecting needle tip, that effectively reduces the risks that a person handling the hypodermic needle will make contact with the needle tip. A hypodermic needle typically includes a barrel with a plunger to displace fluid in the barrel through a projecting hollow needle or cannula having a sharp needle tip formed by a bevel at the end of the cannula. Specifically, when used this invention automatically places a protective sleeve around the cannula as the plunger is displaced, with an outer edge of the sleeve moving toward the needle tip to or slightly beyond the bevel of the cannula once the injection is completed.

The threat of transmission of infectious disease through accidental contact with used hypodermic needles has forced health care workers to increase safety procedures. Despite these precautions, it is estimated that over 200 health care workers have contracted the AIDS virus through accidental contact with contaminated needles. No estimated number of hepatitis transmissions appears to have been documented, but it is likely that the actual number of transmissions is equal to or greater in magnitude to the number of AIDS virus transmissions.

Unfortunately, diseases are transmitted via infected, ordinary hypodermic needles in other ways. Each year, many illicit drug users are infected with diseases such as hepatitis and the AIDS virus through reuse of infected needles. News reports often contain cases of individuals, typically children, being accidentally pierced by used hypodermic needles that find their way into the environment.

The prior art consists of a syringe with a sheath device that attempts to provide protection from accidental piercings but is incapable of providing protection from the problems described above. These deficiencies are primarily the result of the failure of the sheath to automatically engage during the injection process and the lack of an effective locking mechanism to lock the sheath in place over the needle. Accidental piercing may occur after injection when attempting to move the sheath of the prior art device over the exposed needle.

SUMMARY OF THE INVENTION

The protective sleeve is fitted to the hypodermic needle of this invention and solves many of the inherent limitations noted above. As described in the preferred embodiment of the invention, the addition of the protective sleeve significantly reduces the risks of disease transmission in a novel and practical manner.

It is contemplated that ordinary syringes or hypodermic needles could be easily fitted with the protective sleeve, and that only minor manufacturing changes in production of the ordinary hypodermic needle would be necessary to produce a safe syringe comprising a hypodermic needle having a protective sleeve.

Once manufactured, the hypodermic needle with the protective sleeve offers additional and unique advantages to persons who ship or otherwise handle empty hypodermic needles, because the protective sleeve of this invention automatically encompasses the cannula when the plunger is fully depressed and the barrel is void of any drug.

The sleeve-protected hypodermic needle of this invention resembles an ordinary hypodermic needle, and users would immediately recognize the increased safety provided by the protective sleeve, but would detect little or no difference in function when the invention is used to administer intramuscular drugs such as vaccines or antibiotics.

In use, the user first selects a new sleeve-protected fitted hypodermic needle from the location where such instruments are stored. As with the ordinary hypodermic needle, the invention is hermetically sealed inside a bag, typically clear plastic. If the syringe is pre-filled with a drug solution, it is anticipated that the cannula will included a temporary, hard protective plastic covering, as is commonly included with ordinary hypodermic needles. The user removes and discards this protective covering immediately prior to injection into the subject.

If the invention is shipped lacking a pre-filled drug solution, then after removal of the non-permeable bag, the user immediately inserts the cannula into a vial or ampule containing the desired drug solution to then aspirate the drug solution into the barrel by withdrawing the plunger. It is anticipated that the inner diameter and thickness of the sleeve will be sufficient to allow insertion of the cannula into the vial before the plunger is retracted.

At this point the user injects the drug solution into the subject. As the plunger is depressed, the end of the sleeve moves towards the bevel at the end of the cannula, and, at the end of the plunger stroke, the distal end of the sleeve stops at or slightly beyond the bevel locks in its extended position.

After the injection is completed, the safety syringe is spent and is discarded. Although special, expensive sterilization procedures may be undertaken to reuse syringes, modern practice dictates that syringes are customarily discarded after a single use.

In most hospital environments it is likely that the safety syringe will be discarded after use. It is in this situation that the preferred embodiment of the invention offers significant safety advantages over the prior art. In the preferred embodiment, the locking means will engage immediately after completion of the injection. The protective sleeve is locked into place, significantly reducing the likelihood that the user or disposal personnel will make contact with the bevel.

It is an unfortunate fact that disposed medical instruments often end up located far away from their proper disposal location and can be found in landfills, on beaches, and even in playgrounds. It is another unfortunate fact that many illicit drug users reuse and share ordinary hypodermic needles without first properly sterilizing their instruments.

The preferred embodiment of this invention will significantly eliminate the chances of unintentional contact when the invention is discarded in an improper environment and discovered by a curious, typically young, passerby. Similarly, the preferred embodiment of this invention would significantly eradicate the transmission of disease among illicit drug users because reuse of the invention is made impractical.

These and other features will become apparent from a consideration of the Detailed Description of the Preferred Embodiments.

DETAILED DESCRIPTION OF THE PREFERRED EMBODIMENTS

Figure 1:
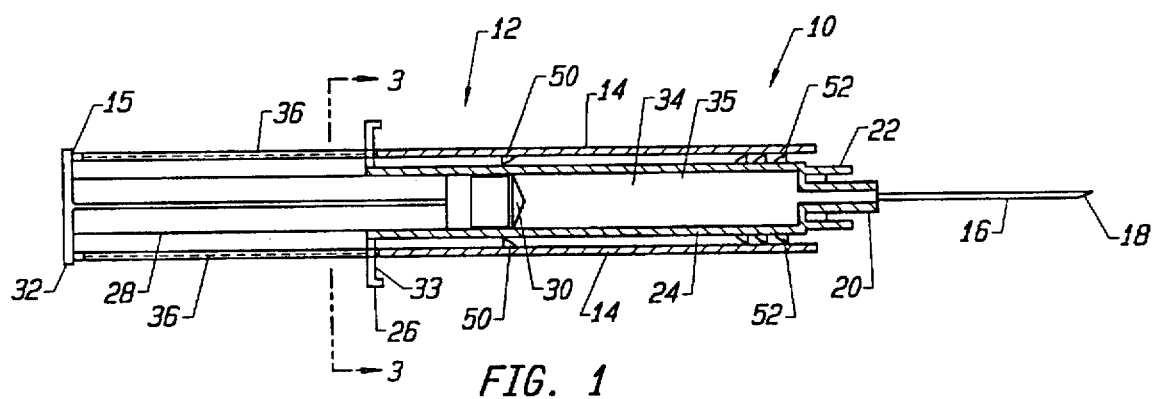
FIG. 1 is a side cross-sectional view of a hypodermic needle with a protective sleeve and a plunger in retracted position.

Referring to FIG. 1, the safety syringe of this invention, designed by the reference numeral 10 comprises a hypodermic needle 12 with a protective sleeve 14 forming a unitary device. The safety syringe in FIG. 1 is shown ready for use on a subject. The hypodermic needle 12 includes a needle member comprising a hollow cannula 16 that terminates with a bevel 18 forming a sharp tip 19. The other end of the cannula 16 is attached to a socket 20. The socket 20 is joined to a projecting tip 22 at one end of a barrel 24 of the hypodermic needle 12. The other end of the barrel 24 is open and terminates with a barrel flange 26. A plunger 28 having an elastomeric seal 30 is inserted into the open end of the barrel 24 forming a chamber 25 within the barrel 24. A plunger flange 32 is located on the end of the plunger 28 opposite the elastomeric seal 30.

Typically, a pharmaceutical fluid 34 located in the chamber 25 inside the barrel 24 is forced out of the unit 10 through the bevel 18 when the plunger 28 is depressed towards the tip 22 of the barrel 24. In the conventional hypodermic needle lacking the protective sleeve, the cannula and bevel remain fully exposed after the fluid has been fully expelled from the barrel, making the conventional hypodermic needle a contaminated instrument easily capable of transmitting disease if the exposed needle tip punctures skin.

Figure 2:
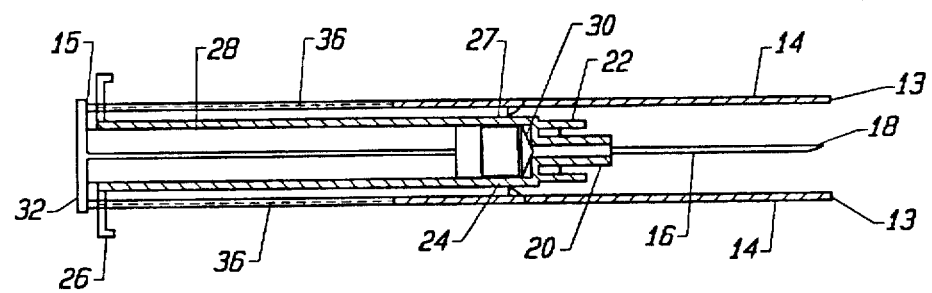
FIG. 2 is a side cross-sectional view of the hypodermic needle of FIG. 1 with the protective sleeve and plunger in extended position.
Figure 3:
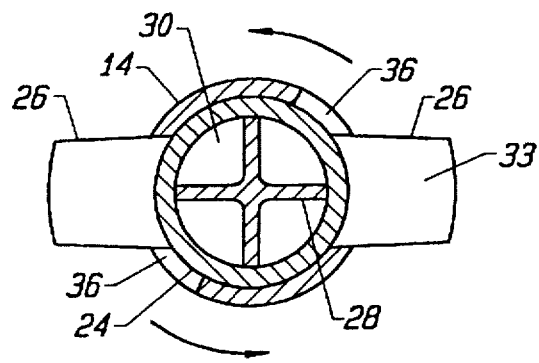
FIG. 3 is an enlarged cross-sectional view taken on the lines 3—3 in FIG. 1.

In the preferred embodiment shown in FIGS. 1-3, the protective sleeve 14 has a cylindrical shape having one end 15 affixed to the plunger flange 32 and encompasses both the plunger 28 and the barrel 24. Side slots 36 are cut into the protective sleeve 14 lengthwise from the plunger flange 32 to the barrel flange 26 to accommodate projecting flange elements 33 on the barrel 24 as shown in FIG. 3, thus allowing the plunger 28 to freely travel through its ordinary range of motion. The plunger flange 32 and the barrel flange 26 provide for the positioning of the user's fingers and thumb, respectively, when injecting a drug.

The length of the protective sleeve 14 is selected such that the end opposite the plunger flange 32 protrudes slightly past the bevel 18 when the plunger 28 has been fully depressed towards the tip 22. When the unit 10 is placed in this protective configuration, as illustrated in FIG. 2, the circular edge of the protective sleeve 14 makes first contact with any smooth surface placed close to the bevel 18 and greatly reduces the risk of the bevel 18 puncturing the surface.

It is expected but not required that the unit will be shipped to user in its protective configuration. The user, typically a health care provider, will fill the inside of the barrel 24 with the pharmaceutical fluid 34 by inserting the bevel 18 and part of the cannula 16 into an ampule or vial containing the pharmaceutical fluid 34 and then pulling the plunger flange 32 away from the tip 22. The pharmaceutical fluid 34 is drawn into the inside of the barrel 24 through a process known as aspiration.

Figure 4A:
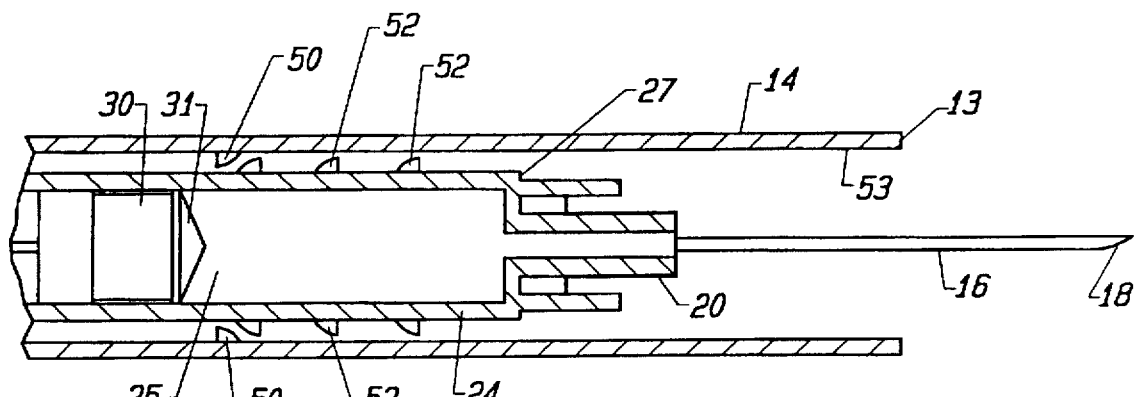
FIG. 4a is an enlarged schematic view of the locking mechanism in the hypodermic needle of FIG. 1.
Figure 4B:
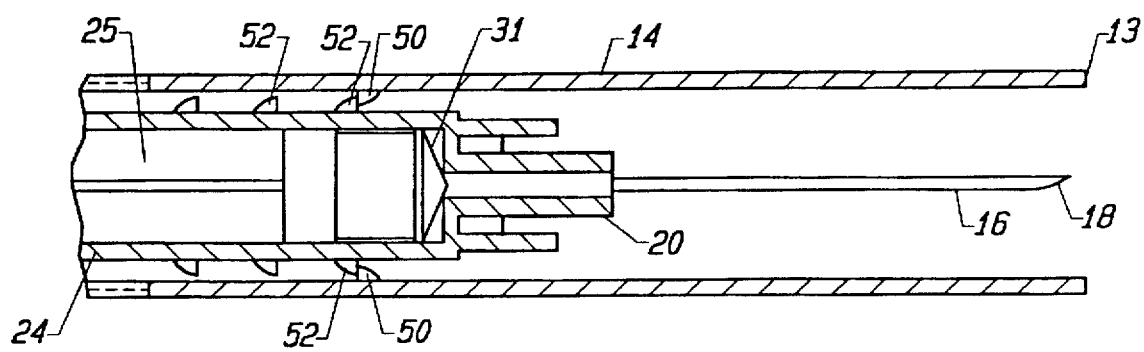
FIG. 4b is an enlarged schematic view of the locking mechanism in the hypodermic needle of FIG. 2.

The preferred embodiment also includes locking means allowing the user to automatically lock the unit in the protective configuration shown in FIG. 2 after delivery of the pharmaceutical fluid 34 is completed. The locking means is schematically illustrated in FIG. 4a and 4b.

In the preferred embodiment, two sleeve pawl members 50 are placed on the inner surface 53 of the protective sleeve 14 one-hundred eighty degrees apart and close to the tip 31 of the elastomeric seal 30. Two sets of barrel teeth members 52 are placed on the outer surface 27 of the barrel 24 one-hundred eighty degrees apart and close to the tip 22.

The sleeve pawl members 50 and barrel teeth members 52 are sized so as not to hinder the movement of the plunger 28 and protective sleeve 14 along the surfaces of the barrel 24, until the sleeve pawl members 50 make contact with the barrel teeth members 52. When contact is made the teeth and pawl members 50 and 52 click into engagement, locking the sleeve 14 to the barrel 24.

Whether the unit 10 is shipped to the user empty of pharmaceutical fluid 34 or prefilled with pharmaceutical fluid 34, it is expected that the unit will be set in its "unlocked" position. In the unlocked position, the plane formed by the sleeve pawl members 50 is slightly angled away from the plane formed by barrel teeth members 52. Thus the sleeve pawl members 50 will not engage with the barrel teeth members 52 when the unit 10 is placed in its protective configuration.

To engage the locking means, immediately prior to usage of the unit 10, the user aligns the sleeve pawl members 50 into the same plane as the barrel teeth members 52 by slightly twisting the end of the protective sleeve 14 located next to the plunger flange 32 as shown by the directional arrow in FIG. 3. FIG. 4a illustrates the protective sleeve 14 and locking means as the injection is being delivered.

It is anticipated that shortly before the injection is completed, the end 13 of the protective sleeve 14 will make contact with the subject's skin until injection is delivered and the needle tip is withdrawn from the subject. In this manner, the sleeve is located in its protective position at the time the injection process is completed.

The sleeve pawl members 50 pass over the barrel teeth members 52 and each sleeve pawl member mates with one barrel tooth 52, effectively locking the protective sleeve 14 in its protective configuration, as illustrated in FIG. 4b.

What is claimed is:

1. In a hypodermic needle including a hollow barrel for containing a pharmaceutical fluid, and an elongated, displaceable plunger in the barrel, the barrel having a tip end with a needle cannula with an end bevel, a flange end with an opening for the displaceable plunger and means on the barrel for manipulating the barrel relative to the plunger, the improvement comprising a protective sleeve connected to the displaceable plunger, the plunger having opposite ends with a seal at one end and a flange at the other, the protective sleeve including:

a substantially cylindrical sleeve member encompassing both the plunger and the outer surface of the barrel, the sleeve member having one end secured to the plunger proximate the flange end and another and terminating at the end of the bevel when the plunger is fully displaced relative to the barrel for delivery of the pharmaceutical fluid.

2. The improved hypodermic needle of claim 1 wherein the sleeve member has an inner surface and the barrel has an outer surface, and further including locking means for locking the inner surface of the sleeve member to the outer surface of the barrel when delivery of the pharmaceutical fluid is complete for preventing reuse of the hypodermic needle.

3. The improved hypodermic needle of claim 2, with disengagement means for disengaging the locking means prior to the initial depression of the plunger.

4. A hypodermic needle having a protective sleeve, the hypodermic needle comprising:

a barrel means for containing a pharmaceutical fluid, the barrel means having a first open plunger end and a second needle end with a projecting needle connected to the needle end; and, a displaceable plunger means for displacing pharmaceutical fluid contained in the barrel means, the plunger means having a first end with a seal inserted into the open plunger end of the barrel means and a second end with a flange, the plunger means having an elongated sleeve member secured to the second end, the sleeve member extending over the barrel means and displaceable over the projecting needle when the plunger means is displaced in the barrel means displacing pharmaceutical fluid through the projecting needle, wherein the barrel means has finger engagement means cooperating with the plunger flange for manually displacing the plunger means in the barrel means.

5. The hypodermic needle of claim 1 wherein the barrel means and the sleeve member of the plunger means have interconnecting locking means for locking the sleeve member over the projecting needle when the plunger means has displaced the pharmaceutical fluid from the barrel.

6. The hypodermic needle of claim 1 wherein the sleeve member has side slots and the barrel means has flange elements projecting through the side slots of the sleeve member the flange elements comprising the finger engagement means cooperating with the plunger plunge for displacing the plunger means in the barrel means.

7. The hypodermic needle of claim 6 wherein the projecting flange elements are unitary with the flange end of the barrel.

8. A hypodermic needle having a protective sleeve, the hypodermic needle comprising:

a barrel means for containing a pharmaceutical fluid, the barrel means having a first open plunger end with a flange, and a second needle end with a projecting needle connected to the needle end;

a displaceable plunger means for displacing pharmaceutical fluid contained in the barrel means, the plunger means having a first end with a seal inserted into the open plunger end of the barrel means and a second end with a flange, the plunger means having an elongated sleeve member connected to the plunger flange, wherein the sleeve member has side slots and the flange of the barrel means has flange elements projecting through the side slots of the sleeve member, the sleeve member extending over the barrel means and being displaceable over the projecting needle when the plunger means is displaced in the barrel means displacing pharmaceutical fluid through the projecting needle.

9. The hypodermic needle of claim 8 wherein the barrel means and the sleeve member of the plunger means have interconnecting locking means for locking the sleeve member over the projecting needle when the plunger means has displaced the pharmaceutical fluid from the barrel.

\* \* \* \* \*